United States Patent [19]

Hessner

[11] 4,257,418
[45] Mar. 24, 1981

[54] DEVICE FOR ABSORBING URINE WITH INCONTINENT PERSONS

[75] Inventor: Hans Hessner, Djursholm, Sweden

[73] Assignee: Mo och Domsjo Aktiebolag, Ornskoldsvik, Sweden

[21] Appl. No.: 21,602

[22] PCT Filed: Jan. 22, 1979

[86] PCT No.: PCT/SE78/00005

§ 371 Date: Feb. 23, 1979

§ 102(e) Date: Jan. 22, 1979

[87] PCT Pub. No.: WO 79/00008

PCT Pub. Date: Jan. 11, 1979

[51] Int. Cl.³ .............................................. A61F 5/44
[52] U.S. Cl. ................................................... 128/286
[58] Field of Search .............. 128/284, 286, 287, 288, 128/290 H, 291, 295

[56] References Cited

U.S. PATENT DOCUMENTS

| | | | |
|---|---|---|---|
| 2,104,423 | 1/1938 | Hughes | 128/286 |
| 2,277,043 | 3/1942 | Cohn | 128/286 |
| 2,431,571 | 11/1947 | Lehr | 128/295 |
| 2,711,736 | 6/1955 | Petitpas | 128/286 |
| 3,172,817 | 3/1965 | Leupold et al. | 128/284 |
| 3,211,147 | 10/1965 | Pherson et al. | 128/284 |
| 3,212,500 | 10/1965 | Bardy | 128/286 |
| 3,306,293 | 2/1967 | Marder et al. | 128/284 |
| 3,522,808 | 8/1970 | Worcester | 128/286 |
| 3,670,731 | 6/1972 | Harmon | 128/284 |

Primary Examiner—C. Fred Rosenbaum

[57] ABSTRACT

A device for absorbing urine with incontinent persons is disclosed, which device comprises a holder for multiple use and a disposable diaper situated in the holder. The holder consists of a perforated inner part made from a thin flexible material and an outer part also made from a thin flexible material. The inner part has a curved shape to bear against the bodily shape of the wearer and includes an upwardly wider portion in relation to the wearer and a downwardly tapering portion. Running along its outer contours is a reinforcement made from a flexible material having such stability that a curved form is maintained. The outer part is of substantially the same shape as the inner part and is attached to the downwardly tapering portion of the inner part. The outer part also has a reinforcement running along its outer contour. The diaper has an extension corresponding to that of the inner part of the holder and comprises an absorption core and a liquid-permeable material enveloping the absorption core. The inner part may be shaped substantially as an equilateral triangle and may have a rectangular extension.

14 Claims, 8 Drawing Figures

DEVICE FOR ABSORBING URINE WITH INCONTINENT PERSONS

The present invention relates to a device for collecting and looking after urine for persons with difficulty in controlling urination. This problem is technically known as urinary incontinence and is a severe psychic and hygienic problem for the persons afflicted with it. Usually elderly men are the ones vexed by this ailment, and the device according to the invention is especially suitable for them, but is also utilizable by other incontinent persons, e.g. women.

Previously, these persons have been mainly dependent on the same type of diaper used by children. Special diapers for incontinence are manufactured, but the main difference between these and children's diapers is the size. Conventional diapers, as intended here, are type disposable type and have different design and construction.

One type of diaper is quadrilateral and consists, for example, of fluffed-up cellulose wadding enveloped by soft paper and/or non-woven fibre. The diaper side facing away from the wearer is completely covered by a plastic coating. This type of diaper can possibly be provided with edge recesses for the wearer's legs. Such diapers are sometimes called all-in-one diapers. In using them, however, large sections of the wearer's skin will be enclosed by the absorption body and the liquid-tight plastic coating, which causes the diaper to function as a wet poultice. This can very easily lead to skin trouble for the wearer and, furthermore, to an unpleasant odor. These problems are serious with children and even more serious with incontinent persons, which is explained by urine volume being greater for adults. Another type of diaper is also common, namely one with a width which is considerably less than its length and thus has a rectangular shape. Such diapers are used together with a plastic diaper protector, usually in the shape of a triangle, which has a greater surface area than the diaper itself. When using such a diaper, the surface of the wearer's trunk coming into contact with the wet absorption body is indeed reduced, but because of the enveloping plastic triangular protection this diaper also functions as a wet poultice, although to a lesser extent than in the former case. Such a diaper is also burdened with the disadvantage that it is displaced downwards and backwards, due to the movements of the wearer, which is unfortunate since urination always takes place forwardly. A solution of this latter problem has, however, been proposed in the Swedish Patent Application No. 1680/70, describing a diaper, one end of which has a widening transverse portion which is intended to be positioned in front of the wearer's legs and is stable in shape in a wet as well as in a dry condition. However, this diaper is also burdened with disadvantages. Amongst other things it has a high price due to the reinforcement of the diaper, which must be made so that it retains its shape even when wet. This diaper is indeed intended to be used together with a pair of pants which are liquid-and gas-permeable, i.e. they can "breathe", but due to the relatively large surface area of the diaper there will still be a considerable part of the wearer's trunk which comes into direct contact with the wet absorption body. Apart from the above-mentioned disadvantages, all the diapers mentioned so far, i.e. diapers which are primarily intended to be used by children, have the great disadvantage that they are intended for collection of both urine and faeces. It has been found unsuitable for incontinent persons to use one and the same absorption device for collecting urine and faeces. This is in connection with the occurrence of an unsuitable mixture of bacteria in such cases. Those skilled in the art have therefore arrived at the opinion that there is a special need for an absorption device for persons suffering from urinary incontinence, which is definitely different from conventional diapers. This has resulted in there being such an absorption device on the market today. This device is very much like a bag, the side of which facing away from the wearer being longer than the side facing towards the wearer. These sides are united with each other so that a compartment or space for collecting urine is formed. Since the device consists of absorbent material, the urine is absorbed and retained in this material. However, this absorption device also has disadvantages. Among other things, due to its construction it also has a high price. Furthermore, it would appear difficult to achieve a seal between the absorption device and the body of the wearer. This can result in the occurrence of an unpleasant odor.

The present invention has the object of solving the problems discussed above, and relates to a device for absorbing urine adapted to be worn by adults incontinent, comprising a holder for multiple use and a disposable type diaper fitting in the holder and removably carried by the holder. The device is characterized in that the holder has a perforated inner part made from a thin flexible material with a curved shape, bearing agains the body shape of the wearer with an upwardly wider portion in relation to the wearer, and a downwardly tapering portion with reinforcement made from a flexible material running along the outer contour of the part, said material having such stability that a curved form is maintained; and an outer part of thin flexible material with substantially the same shape as the inner part and attached to the downwardly tapering portion of the inner part, said outer part having reinforcement running along its outer contour; and tha the diaper has a shape corresponding to that of the inner part, and is built up from an absorption core and a liquid-permeable material enveloping the absorption core.

The invention will now be described in detail in the following while referring to the embodiments of the absorption device shown on the attached drawings.

As stated previously, the absorption device according to the invention is compound of two parts, a holder 1 in which a diaper 2 is placed. The holder will be of such material that it can be used several times, e.g. at least during a period of two months. On the other hand, the diaper is of the disposable type, i.e. it is thrown away after use. This means that several diapers are consumed from day to day. With regard to the shape of the holder and diaper, these have a hand-in-glove relationship.

Figure 1:
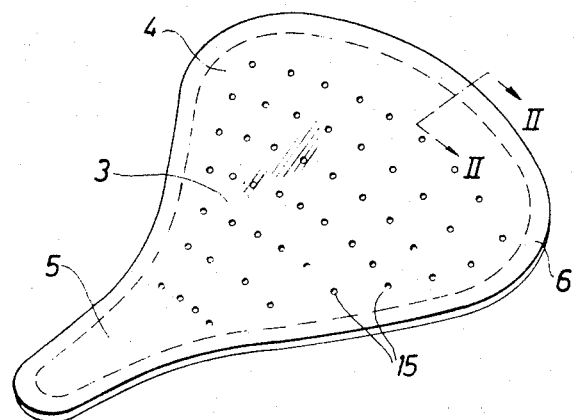
FIG. 1 shows the inner part of a first embodiment of a holder according to the invention.
Figure 3:
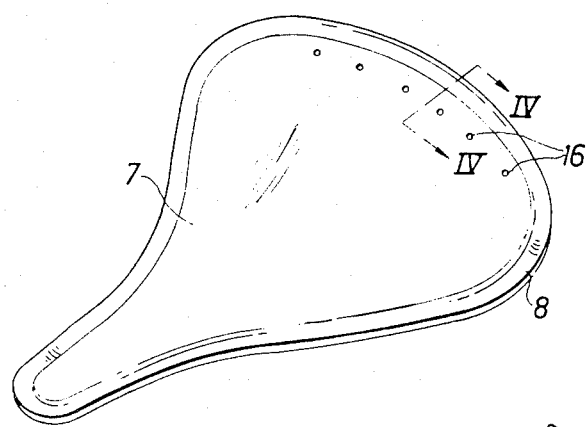
FIG. 3 shows the outer part of the first embodiment of a holder according to the invention.

In FIGS. 1 and 3 there are shown the inner part and outer part, respectively, of a holder according to a first embodiment of the invention, these two parts being separated from each other. In reality these two parts are attached to each other at the tapering portion 5 of the inner part to form a holder, as is apparent from FIG. 5. This separation of the inner part and outer part of the holder into two separate figures has been done to facilitate understanding the invention. The inner part 3 shown in FIG. 1 is composed of a thin flexible material with a curved form, which bears against the body shape of the wearer. The inner part 3 has a portion 4, upwardly wider in relation to the wearer, and as stated above, a downwardly tapering portion 5. Reinforcement 6 runs along the outer contour of the inner part 3. This reinforcement 6 consists of a flexible material with such stability that a curved shpae is maintained, which enables a sealing abutment of the inner part of the holder against the body of the wearer. The inner part 3 is provided with a relatively large number of perforations 16, enabling the passage of urine through the inner part. The shape, pattern and number of perforations can be varied. With regard to shape, substantially round perforations are preferred. The number and size of the perforations are chosen so that urine is allowed to pass through the inner part 3 practically instantaneously. The majority of the perforations are made in the upper portion of the inner part. The inner part 3, and thereby also the holder 1, have a configuration in the form of an equilateral triangle with rounded corners.

Figure 2:
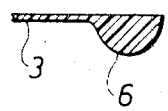
FIG. 2 shows a cross-section denoted by II—II in FIG. 1 showing a reinforcement running round the outer configuration of the holder inner part.

FIG. 2 shows a cross-section denoted by II—II in FIG. 1 of the reinforcement 6. This has a substantially semi-circular cross-section, and the flat end of the reinforcement is intended to rest against the wearer's body. The material thickness of the reinforcement 6 is several times as great as the material thickness of the rest of the inner part 3. The task of the reinforcement is to keep the diaper in place sideways and in height, and also to form a sealing abutment to the wearer.

FIG. 2 shows an outer part 7 of thin flexible material with substantially the same form as the inner part 3. Along the outer contour of the outer part 7 there is also reinforcement 8. According to a preferred embodiment, the outer part 7 is completely impervious to liquid. It is, however, conceivable to perforate the outer part 7 also. These perforations 16 are few and must be placed just under the reinforcement 8 in the upper portion of the outer part. The reason for making the perforations 16 so high up on the outer part 7 is that the risk of urine penetration must be obviated. When the outer part 7 is provided with perforations 16, a modified diaper should be used to avoid possible embarrassing smells, and this diaper is described in detail further on in the text. A holder with an outer portion provided with perforations may be necessary for persons having especially sensitive skin.

Figure 4:
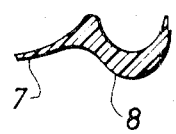
FIG. 4 shows a cross-section denoted by IV—IV in FIG. 3 of a reinforcement at the outer part of the holder running round the outer contour.

FIG. 4 shows a cross-section denoted by IV—IV in FIG. 3 of the reinforcement 8. This reinforcement has a cross-section adapted for sealing connection to the reinforcement 6. The material thickness of the reinforcement 8 is greater than that of the rest of the outer part 7, although the difference does not need to be so pronounced as between the reinforcement 6 and the inner part 3. The holder 1 is shown complete in FIG. 5, i.e. as it is used. The inner part 3 and the outer part 7 are, as previously mentioned, sealingly united at the downwardly tapering portion 5 of the inner part. A liquid-tight pocket is thereby formed in the lower portion of the holder. This pocket is of great importance if the volume of urine of the incontinent person is so heavy that urine is not instantly absorbed by the diaper in the holder. The domed or curved shape of the holder is apparent from FIG. 5, this shape accommodating itself to the body shape of the wearer, It is primarily the reinforcement 6 which provides the sealing closure to the wearer, to prevent urine from leaking out past the side of the holder. However, the thinner material in the inner part 3 also bears against the body of the wearer to a certain extent, i.e. the zone of the inner part 3, which is in direct contact with the reinforcement 6. The inner part 3 is otherwise not substantially in direct contact with the wearer's body, which is apparent from FIG. 5, where the holder is shown from one side. The intention with the absorption device according to the invention is that there shall be no direct contact between the wearer and the diaper and that direct contact between the holder and the wearer is reduced as far as possible. The outer part 7 with its reinforcement 8 are complementary in shape and in connection with the inner part 3 with its reinforcement 6. When the holder is closed, i.e. when the reinforcement 8 is connected to the reinforcement 6, a space is formed in the holder corresponding to the shape and volume of the diaper according to the invention. When the holder with inserted diaper is placed on the wearer, it shall be placed with the wider portion upwards and the narrower portion between the wearer's legs. So that the holder shall fit well to the wearer, it has been found suitable to form the narrow part of the holder so that it has indentations corresponding to the shape of the inner side of the wearer's legs. This is apparent from FIG. 1 as well as FIG. 3. The fit between the reinforcement 8 on the outer part 7 and the reinforcement 6 on the inner part 3 prevents leakage of possible excess urine. It has furthermore been found that this fit facilitates changing diapers, since the inner part reinforcement strives to come into the outer part reinforcement, or vice versa.

The reinforcement of the inner part and outer part of the holder does not necessarily need to have the cross-section as seen in FIG. 2 and FIG. 4, respectively. For example, the reinforcement of the holder inner part can be so shaped that the semi-circular cross-section is turned with its round surface towards the wearer's body. This further reduces the contact area between the wearer's body and the holder. The reinforcement of the holder outer part is adapted so that a sealing enclosure is obtained. Furthermore, the reinforcement on both inner and outer parts can be formed so that a rectangular cross-section is made.

The holder according to the invention is not limited to the configuration shwon in FIGS. 1 and 3. A holder can thus be conceived wherein the upper wider portion has a rectangular shape while the narrower portion, similar to the holder according to FIGS. 1 and 3, has indentations corresponding to the shape of the inner sides of the wearer's legs. Such a holder corresponds to, and accommodates the diaper 2 shown in FIG. 7. However, the holder can have a configuration lying between or somewhat different from the configuration of the latter holder and the configuration of the holder according to FIGS. 1 and 3. For all holders it is, however, a requirement that they shall have an upwardly wider portion and a downwardly tapering portion in relation to the wearer.

Furthermore, the corners and edges of the holder must be rounded off and as anatomically correct as possible. If this condition is not complied with, the holder will not fit against the wearer's body and furthermore, there is risk that the holder will chafe against the wearer's skin.

Figure 5:
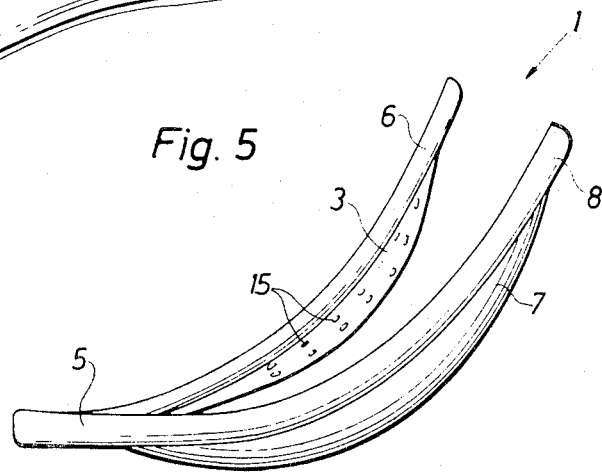
FIG. 5 shows a holder in its entirety seen from one side according to a first embodiment, i.e. according to the FIGS. 1-4.

The inner and outer parts of the holder consist, as previously mentioned, of a thin flexible material and a thicker flexible material along the periphery, this material being designated reinforcement or bead. The inner and outer parts can each be formed (e.g. molded) in one piece or built up from a thin material on which a separate reinforcement or bead has been attached. The material from which the reinforcement is built must have such stability and thickness that the domed or curved shape shown in FIG. 5 is maintained. Furthermore, the material must be supple and elastic so that sealing conformity to the wearer is achieved, even if the anatomy of the wearer varies. The remaining portions of the inner and outer parts will preferably consist of the same material, although with considerably less thickness. As an example, thermoplastic material can be mentioned. Silicone plastic has been found to be especially utilizable. An example of such a silicone plastic is silicone rubber. The holder must be of such material that it is easy to clean after use, e.g. in warm water. The material must also withstand urine, i.e. it must not become discoloured or degenerate in some other way.

Figure 6:
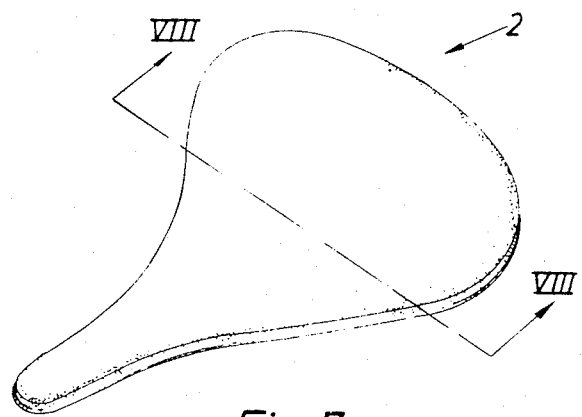
FIG. 6 shows a first embodiment of a diaper according to the invention.
Figure 8:
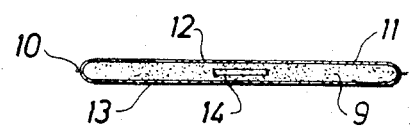
FIG. 8 shows a cross-section denoted by VIII–VIII of a diaper according to FIG. 6.

FIG. 6 shows a diaper 2 which fits the holders according to FIG. 5. FIG. 8 shows this diaper in cross-section. The diaper consists of an absorption core 9 and an enveloping liquid-permeable material 10. Several different materials can be used as absorbants, although fluffed cellulose wadding is preferred. In order to improve the ability of the diaper to spread out urine over the greater portion of itself, and thereby increase its absorption ability, a strip 14 of highly absorbent material. e.g. of carboxyalkylcellulose type, can be introduced. Such a strip extends along the diaper, although not right out to the edges, since there is then risk of leakage. Mild chemical preparations can also be mixed into the absorption body to prevent the spread of bacteria and thereby reduce the problem of smells. Such a diaper should be used in the case where there are a few perforations 16 made in the outer part 7 of the holder 1. A layer 11 of soft paper can be applied round the absorption body, which is in the form of fluffed cellulose wadding, for example. This layer is not absolutely necessary and can be dispensed with. The liquid-permeable layer 10 surrounding the absorption body can be any of several materials. As examples can be mentioned non-woven mat and soft paper. The surrounding layer 10 can consist of one and the same material, or of an upper layer 12 and a lower layer 13, attached to each other along the periphery of the diaper. According to a preferred embodiment the diaper of "flushable" i.e. it can be flushed down a toilet without inconvenience. From this point of view it is most suitable that both layer 12 and layer 13 consist of soft paper. The upper layer 12 should preferably consist of wet-strength soft paper, i.e. soft paper provided with wet-strength resin. The upper layer 12 can also consist of non-woven fibre, this material having greater strength and resistance than wet-strength soft paper, especially after being wetted. Apart from the above-mentioned embodiments, the diaper can be completely surrounded by non-woven fabric or wet-strength soft paper.

Figure 7:
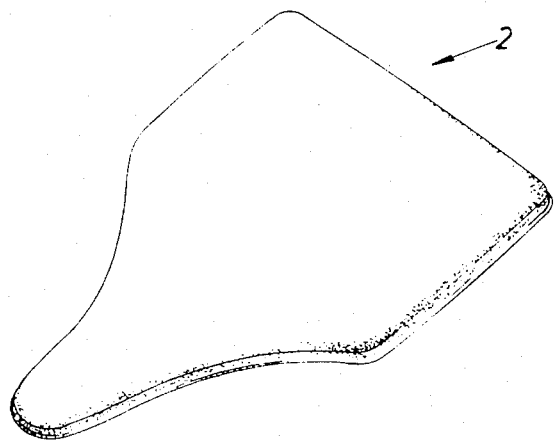
FIG. 7 shows a second embodiment of a diaper according to the invention.

The diaper shown in FIG. 7 distinguishes from the diaper a FIG. 6 only with respect to the shape. The construction of both diapers is the same.

With regard to the proportions of the diaper according to the invention in comparison with conventional diapers, the following can be stated. The most usual diaper in Scandinavia, i.e. the elongate, rectangular type, has a width of about 10-13 cm and a length of about 30-40 cm. The proportions of the diaper according to the invention can naturally be varied, but as an example it can have a width of about 16 cm and a length of about 17 cam. The thickness of the diaper can also be varied, but preferably should not exceed 12-15 mm. According to a preferred embodiment, the diaper is of uniform thickness, although it can be made thicker in the middle in its longitudinal direction, and its central portion can also be made thicker than the rest of it.

With regard to the shape of the diaper, this can be varied in a similar way to that in which the holder shape is varied. Since the diaper is to fit into the holder, the form of the diaper must be suited to the form of the holder, and vice versa. It is, however, the intention to form the diaper as far as possible so that it can be punched out from a rectangular, continuous web in a way which minimizes material waste. This can be achieved by having adjacent punching tools facing in opposite direction, i.e. diapers are punched so that the wide portion of one diaper is in the region of the narrower portion of the diapers on either side thereof, or in other words, the diapers are punched out zig-zag.

For persons with unusually large urination, and then preferably for night-time use, it can be necessary to attach a plastic tube liquid-tight to the narrower portion of the holder to takeaway excess urine, i.e. the amount of urine the diaper cannot take care of. It is further conceivable to attach some kind of vacuum pump to the plastic tube for facilitating removal of excess urine. Connecting a plastic tube to the holder is not the normal case but can be resorted to in extra difficult conditions. The absorption device according to the present invention. i.e. the holder and a diaper therein, is intended for use in combination with ordinary textile underpants. Special underpants, possibly containing plastic, are not required since the holder is liquid-tight per se. The application of the absorption device is quite simply carried out by pulling out the trouser waist from the body, whereon the absorption device is pushed down into the underpants with the narrower part between the wearer's legs and bearing against the insides of them. Due to its shape and the pressure of the underpants, the absorption device is retained in the right portion so that leakage of urine is avoided.

The absorption device according to the invention has many advantages, and is intended to facilitate incontinent persons, usually elderly men, living with their problems with the least possible discomfort. The absorption device is designed so that leakage of urine is avoided. Direct engagement of the diaper against the body is also prevented. The feeling of freedom from incontinence is thereby substantially improved for the wearer. The device is easy to change, i.e. take off and put on. This is an important advantage especially for elderly people. Due to the sealing engagement between the holder and the wearer, the risk of embarrassing smells is reduced.

I claim:

1. A device for absorbing urine adapted to be worn by incontinent adults, comprising a holder for multiple use, and a disposable diaper separate from but suited to and removably carried in the holder, the holder having a perforated inner part of a thin flexible material with a curved shape, bearing against the body shape of the wearer, with an upwardly wider portion in relation to the wearer and a downwardly tapering portion with reinforcement of a flexible material running along the outer contours, said material having such stability that a curved form is maintained; and an outer part of thin flexible material with substantially the same shape as the inner part and attached to the downwardly tapering portion of the inner part, said outer part having reinforcement running along its outer contour; and the diaper being retained between the inner and outer parts and having a shape corresponding to that of the inner part, and being composed of an absorption core and a liquid-permeable material enveloping the absorption core.

2. A device as claimed in claim 1, in which the inner part has an extension substantially in the shape of an equilateral triangle with rounded corners.

3. A device as claimed in claim 1, in which the wider portion of the inner part has a rectangular extension.

4. A device as claimed in any of claims 1, 2 or 3, in which the tapering portion of the inner part has indentations corresponding to the shape of the inner sides of the wearer's legs.

5. A device as claimed in any of claims 1, 2, or 3 in which the downwardly tapering portion of the inner part and the corresponding portion of the outer part are sealingly attached to each other to form a liquid-tight pocket in the lower part of the holder.

6. A device as claimed in any of claims 1, 2, or 3 in which the perforations are in the upper portion of the inner part.

7. A device as claimed in any of claims 1, 2, or 3 in which the reinforcement has a substantially semi-circular cross-section.

8. A device as claimed in claim 7, in which the semi-circular cross-section of the reinforcement has its flat surface facing the wearer's body.

9. A device as claimed in claim 7, in which the seimi-circular cross-section of the reinforcement has its round surface facing toward the wearer's body.

10. A device as claimed in any of claims 1, 2, or 3 in which the reinforcement has a cross-section adapted for sealing connection to the reinforcement.

11. A device as claimed in any of claims 1, 2, or 3 in which the upper portion of the outer part is provided with a few perforations directly under the reinforcement.

12. A device as claimed in any of claims 1, 2, or 3 in which the absorption core of the diaper comprises fluffed cellulose wadding, and the liquid-permeable material comprises nonwoven fabric, at least on the side of the diaper facing the wearer.

13. A device as claimed in any of claims 1, 2, or 3 in which the absorption core of the diaper comprises fluffed cellulose wadding, and the liquid-permeable material comprises wet-strength soft paper, at least on the side of the diaper facing the wearer.

14. A device a claimed in claim 12 in which a strip of absorbent material is inserted in the absorption core.

* * * * *

UNITED STATES PATENT AND TRADEMARK OFFICE
CERTIFICATE OF CORRECTION

PATENT NO. : 4,257,418
DATED : March 24, 1981
INVENTOR(S) : Hans Hessner

It is certified that error appears in the above-identified patent and that said Letters Patent are hereby corrected as shown below:

Column 1, line 19 : delete "type" both occurrences.
Column 2, lines 25 and 26 : "adults incontinent" should be --incontinent adults--.
Column 2, line 31 : "agains" should be --against--
Column 2, line 40 : "tha" should be --that--
Column 2, line 67 : "compound" should be --composed--.
Column 4, line 13 : "," should be --.--.
Column 4, line 39 : "side" should be --sides--.
Column 4, line 60 : "shwon" should be --shown--.
Column 5, line 38 : "absorbants" should be --absorbent--
Column 5, line 57 : after "woven" insert --fibre--.
Column 5, line 61 : "of" should be --is--.
Column 6, line 46 : 'tion." should be --tion,--.

Signed and Sealed this

Thirtieth Day of April 1985

[SEAL]

Attest:

DONALD J. QUIGG

*Attesting Officer*  *Acting Commissioner of Patents and Trademarks*